(12) United States Patent
DeLuca et al.

(10) Patent No.: US 7,214,670 B2
(45) Date of Patent: May 8, 2007

(54) USE OF 2-METHYLENE-19-NOR-20(S)-1α,25-DIHYDROXYVITAMIN $D_3$ TO INCREASE THE LIFE EXPECTANCY OF HUMAN BEINGS

(75) Inventors: Hector F. DeLuca, Deerfield, WI (US); Lori A. Plum, Madison, WI (US); Margaret Clagette-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/669,990

(22) Filed: Sep. 24, 2003

(65) Prior Publication Data

US 2005/0065123 A1    Mar. 24, 2005

(51) Int. Cl.
*A61K 31/593* (2006.01)
*A61K 31/59* (2006.01)
*A61K 31/592* (2006.01)
*C07C 401/00* (2006.01)

(52) U.S. Cl. ...................................... 514/167; 552/653
(58) Field of Classification Search ................ 552/653; 514/167

See application file for complete search history.

(56) References Cited

U.S. PATENT DOCUMENTS 5,843,928 A    12/1998   DeLuca et al.

*Primary Examiner*—Sabiha N. Qazi
(74) *Attorney, Agent, or Firm*—Andrus, Sceales, Starke & Sawall, LLP

(57) ABSTRACT

This invention provides pharmaceutical uses for 2-methylene-19-nor-20(S)-1α,25-dihydroxyvitamin $D_3$. Administration of this compound increases the life expectancy of human beings, especially elderly human beings. In particular, it increases the survival rate of females lacking estrogen, especially post-menopausal females, and reduces mortality resulting from spontaneous development of malignant tumors in both males and females.

5 Claims, No Drawings

USE OF 2-METHYLENE-19-NOR-20(S)-1α,25-DIHYDROXYVITAMIN D₃ TO INCREASE THE LIFE EXPECTANCY OF HUMAN BEINGS

BACKGROUND OF THE INVENTION

This invention relates to vitamin D compounds, and more particularly to pharmaceutical uses for 2-methylene-19-nor-20(S)-1α,25-dihydroxyvitamin $D_3$.

The natural hormone, 1α,25-dihydroxyvitamin $D_3$ and its analog in ergocalciferol series, i.e. 1α,25-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Recently, a relatively new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, an analog which is characterized by the presence of a methylene substituent at the carbon 2 (C-2) has been synthesized and tested. Of particular interest is the analog which is characterized by the unnatural configuration of the methyl group at carbon 20 (C-20), i.e. 2-methylene-19-nor-20(S)-1α,25-dihydroxyvitamin $D_3$. This vitamin D analog seemed an interesting target because the relatively small methylene group at C-2 should not interfere with the vitamin D receptor. Moreover, molecular mechanics studies performed on the model 1α-hydroxy-2-methylene-19-nor-vitamins indicate that such molecular modification does not change substantially the conformation of the cyclohexanediol ring A. However, introduction of the 2-methylene group into 19-nor-vitamin D carbon skeleton changes the character of its 1α- and 3β-A-ring hydroxyls. Both hydroxyls are allylic to the exocyclic methylene group similar to the 1α-hydroxyl group (crucial for biological activity) in the molecule of the natural hormone, 1α,25-$(OH)_2D_3$.

2-methylene-19-nor-20(S)-1α,25-dihydroxyvitamin $D_3$ is known, and this compound exhibits a desired, and highly advantageous, pattern of biological activity which has been reported in DeLuca et al U.S. Pat. No. 5,843,928. This compound is characterized by intestinal calcium transport activity, similar to that of 1α,25-dihydroxyvitamin $D_3$, but exhibiting very high activity, as compared to 1α,25-dihydroxyvitamin $D_3$, in its ability to mobilize calcium from bone. Hence, this compound is highly specific in its calcemic activity. Its preferential activity on mobilizing calcium from bone allows the in vivo administration of this compound for the treatment of metabolic bone diseases where bone loss is a major concern. Because of its preferential activity on bone, this compound would be a preferred therapeutic agent for the treatment of diseases where bone formation is desired, such as osteoporosis, especially low bone turnover osteoporosis, steroid induced osteoporosis, senile osteoporosis or postmenopausal osteoporosis, as well as osteomalacia and renal osteodystrophy.

SUMMARY OF THE INVENTION

The present invention is directed toward various pharmaceutical uses for 2-methylene-19-nor-20(S)-1α,25-dihydroxyvitamin $D_3$. (See formula I and hereinafter referred to as "2-MD") In particular, the present invention demonstrates that administration of 2-MD will substantially increase the life expectancy of human beings, especially elderly human beings. More specifically, 2-MD increases the survival of females lacking estrogen (e.g. post-menopausal females), and reduces mortality resulting from malignant tumors in human beings (both male and female) by inhibiting tumorogenesis in the treatment of a cancer such as skin cancer, lung cancer, leukemia, colon cancer, breast cancer or prostate cancer.

Structurally this 19-nor analog is characterized by the general formula I shown below:

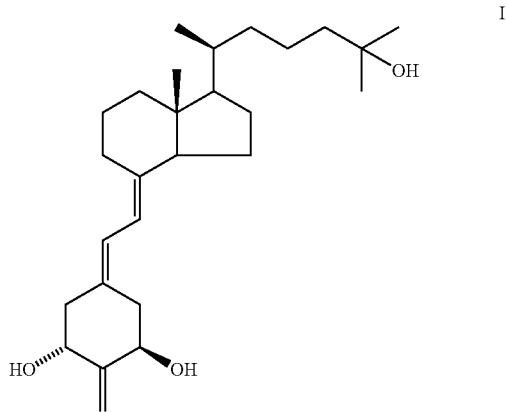

The solid wedge-shaped line to the methyl substituent at C-20 indicates that carbon 20 has the S configuration. The compound may be present in a composition in an amount from about 0.1 μg/gm to about 50 μg/gm of the composition, and may be administered in dosages of from about 0.1 μg/day to about 100 μg/day. The treatment may be transdermal, oral or parenteral.

The above compound is characterized by high cell differentiation activity. Thus, this compound also provides a therapeutic agent for the treatment of malignancies, especially as an anti-tumor agent to inhibit tumorogenesis in persons afflicted with skin cancer, lung cancer, leukemia, colon cancer, breast cancer and prostate cancer.

DETAILED DESCRIPTION OF THE INVENTION 2-methylene-19-nor-20(S)-1α,25-dihydroxyvitamin $D_3$ (referred to herein as 2-MD) was synthesized and tested. Structurally, this 19-nor analog is characterized by the general formula I previously illustrated herein.

The preparation of 2-methylene-19-nor-20(S)-1α,25-dihydroxyvitamin $D_3$ having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1 and C-3 in the latter compound:

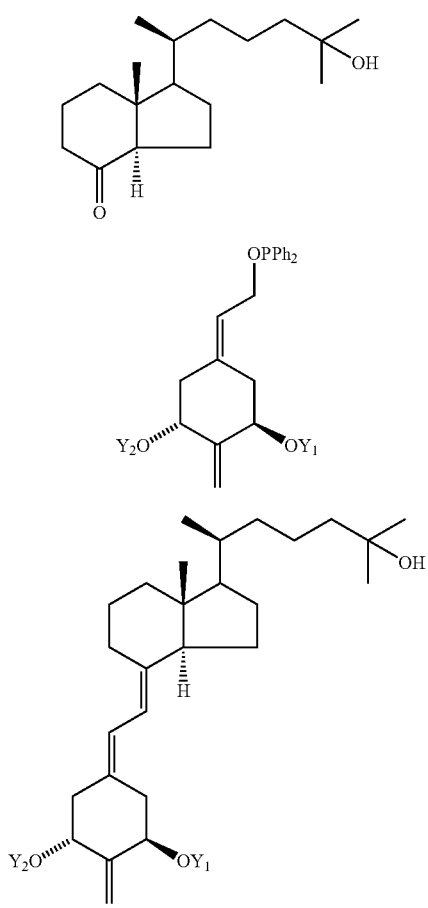

In the structures II, III, and IV groups $Y_1$ and $Y_2$ are hydroxy-protecting groups, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II are known, or can be prepared by known methods.

For the preparation of the required phosphine oxides of general structure III, a new synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compound I is illustrated and described more completely in U.S. Pat. No. 5,843,928 issued Dec. 1, 1998 and entitled "2-Alkylidene-19-Nor-Vitamin D Compounds" the specification of which is specifically incorporated herein by reference. The biological activity of 2-MD is reported in U.S. patent application Ser. No. 09/616,164, filed Jul. 14, 2000, the specification of which is also specifically incorporated herein by reference.

EXAMPLE 1

This example demonstrates that in female rats that have undergone ovariectomy, their survival is significantly increased if they are given 2-methylene-19-nor-(20S)-1,25-(OH)$_2$D$_3$ each day at 5–7 ng/kg/body weight orally. Thus, the experiment was carried out as follows:

48 retired female breeder rats of 12 months of age were obtained from the Harlan Sprague-Dawley Company. Upon arrival, the animals were ovariectomized or sham-operated. These animals were housed in individual hanging wire cages and provided water ad libitum. Food consumption was restricted to 19–21 g/day. Animals were maintained on a purified diet described by Suda et al (J. Nutr. 1970) which contained 0.47% calcium and 0.3% phosphorus. In addition, these animals received supplements of vitamin A, E, D, and K as described in the Suda paper. One half of the animals received each day 0.1 ml of Wesson Oil while the remaining one-half of the animals received orally the 0.1 ml of Wesson Oil containing 5 or 7 ng/2-MD/kg body weight. The animals were monitored weekly for body weight, general health and survival. These animals were followed for 7.5 months. During the course of this period, 4 of the 24 animals receiving the purified diet without supplementation failed to survive largely due to the development of mammary tumors. On the other hand, all animals receiving 2-MD survived the entire period and were in good health.

These results demonstrate that 2-MD increases the survival rate to 100% in the aged, ovariectomized female rats. The mechanism appears to be inhibition of tumorogenesis inasmuch as at least 3 of the controls who failed to survive had developed tumors while the fourth died of unknown causes. The tabular data in Table 1 demonstrate the survival data and also provide the average body weight initially and at 7½ months.

TABLE 1

Suivival and Body Weight in Aged Female Rats

| Treatment | Survival Ratio # premature deaths/total # animals | Body Weight g Initial | Final |
|---|---|---|---|
| Vehicle | 4/24 | 343 ± 6 | 367 ± 10 |
| 2-MD | 0/24 | 361 ± 8 | 382 ± 10 |

For treatment purposes, the compound of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compound may be administered orally, topically, parenterally or transdermally. The compound is advantageously administered by injection or by intravenous infusion of suitable sterile solutions, or in the form of liquid or solid doses via the alimentary canal, or in the form of creams, ointments, patches, or similar vehicles suitable for transdermal applications. Doses of from 0.1 µg to 100 µg per day of the compounds are appropriate for treatment purposes, such doses being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatment of malignancies comprise an effective amount of the 2-methylene-20(S)-19-nor-vitamin D compound as defined by the above formula I as the active ingredient, and a suitable carrier. An effective amount of such compound for use in accordance with this invention is from about 0.01 µg to about 50 µg per gm of composition, and may be administered topically, transdermally, orally or parenterally in dosages of from about 0.1 µg/day to about 100 µg/day.

The compound may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compound is advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of increasing the life expectancy of a post menopausal woman comprising administering to a post menopausal woman an effective amount of 2-methylene-19-nor-20(S)-1α,25-dihydroxyvitamin $D_3$ having the formula:

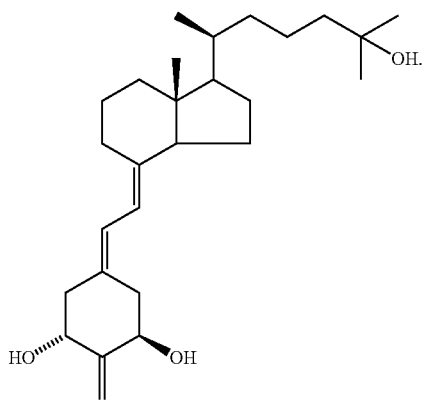

2. The method of claim 1 wherein 2-methylene-19-nor-20(S)-1α,25-dihydroxyvitamin $D_3$ is administered orally.

3. The method of claim 1 wherein 2-methylene-19-nor-20(S)-1α,25-dihydroxyvitamin $D_3$ is administered parenterally.

4. The method of claim 1 wherein 2-methylene-19-nor-20(S)-1α,25-dihydroxyvitamin $D_3$ is administered transdermally.

5. The method of claim 1 wherein 2-methylene-19-nor-20(S)-1α,25-dihydroxyvitamin $D_3$ is administered in a dosage of from about 0.01 µg/day to about 100 µg/day.

* * * * *